US011944107B2

(12) United States Patent
Bush et al.

(10) Patent No.: US 11,944,107 B2
(45) Date of Patent: Apr. 2, 2024

(54) APPARATUS AND METHODS FOR SETTING A GRIND COARSENESS

(71) Applicant: DISMOV PTY LTD, New South Wales (AU)

(72) Inventors: Jake Bush, New South Wales (AU); Clay Bush, New South Wales (AU)

(73) Assignee: DISMOV PTY LTD, New South Wales (AU)

( * ) Notice: Subject to any disclaimer, the term of this patent is extended or adjusted under 35 U.S.C. 154(b) by 408 days.

(21) Appl. No.: 16/652,105

(22) PCT Filed: Oct. 18, 2018

(86) PCT No.: PCT/AU2018/051132
§ 371 (c)(1),
(2) Date: Mar. 30, 2020

(87) PCT Pub. No.: WO2019/109130
PCT Pub. Date: Jun. 13, 2019

(65) Prior Publication Data
US 2020/0305459 A1 Oct. 1, 2020

(30) Foreign Application Priority Data

Dec. 6, 2017 (AU) .................................. 2017904915
Dec. 7, 2017 (AU) ................................ 2017101725

(51) Int. Cl.
*A23F 5/08* (2006.01)
*A23F 5/10* (2006.01)
(Continued)

(52) U.S. Cl.
CPC .................. *A23F 5/08* (2013.01); *A23F 5/10* (2013.01); *A47J 31/525* (2018.08); *G01N 33/14* (2013.01)

(58) Field of Classification Search
CPC ............. A23F 5/08; A23F 5/10; A47J 31/525; G01N 33/14
See application file for complete search history.

(56) References Cited

U.S. PATENT DOCUMENTS 2,720,109 A * 10/1955 Stirn ........................ G01N 9/00
141/73
3,060,724 A * 10/1962 Smith, Jr. ................ G01N 9/02
73/32 R (Continued)

FOREIGN PATENT DOCUMENTS

CN 106361154 * 2/2017
JP H06209709 A 8/1994
(Continued)

OTHER PUBLICATIONS

English Translation for JPH06209709 published Aug. 1994.*
(Continued)

*Primary Examiner* — Anthony J Weier
(74) *Attorney, Agent, or Firm* — Notaro, Michalos & Zaccaria P.C.

(57) ABSTRACT

A method for determining a characteristic of a mass of particulate plant material having the step of determining the density of a mass of particulate plant material, wherein the mass of particulate plant material is prepared from a plant seed, from a coffee bean and/or by grinding a plant material. The invention also relates a system or apparatus for measuring the density of a mass of particulate plant material, wherein the system or apparatus has an experimental vessel having a void configured to retain a mass of particulate plant material therein, volume determination is configured to determine the volume occupied by a mass of particulate plant material that has been disposed within the void of the experimental vessel.

23 Claims, 6 Drawing Sheets

(51) Int. Cl.
  *A47J 31/52* (2006.01)
  *G01N 33/14* (2006.01)

(56) References Cited

U.S. PATENT DOCUMENTS

| | | | | |
|---|---|---|---|---|
| 4,510,808 | A * | 4/1985 | Neville | G01N 9/02 |
| | | | | 177/121 |
| 5,227,188 | A * | 7/1993 | Leppla | A23F 5/10 |
| | | | | 426/454 |
| 5,725,898 | A * | 3/1998 | Murphy | A23F 5/12 |
| | | | | 426/453 |
| 8,479,638 | B2 * | 7/2013 | Leung | A47J 31/44 |
| | | | | 99/302 R |
| 2005/0132890 | A1 | 6/2005 | Constantine et al. | |
| 2012/0048120 | A1 * | 3/2012 | Gillaspie | A47J 42/38 |
| | | | | 99/287 |
| 2012/0196009 | A1 | 8/2012 | Casado | |
| 2014/0370181 | A1 | 12/2014 | Young | |

FOREIGN PATENT DOCUMENTS

| | | | |
|---|---|---|---|
| JP | 2011519584 A | | 7/2011 |
| JP | 2013507209 A | | 3/2013 |
| RU | 1821679 | * | 6/1993 |
| WO | 2009114119 A1 | | 9/2009 |

OTHER PUBLICATIONS

B. R. Corrochano et al: "A new methodology to estimate the steady-state permeability of roast and ground coffee in packed beds", Journal of Food Engineering, vol. 150, Apr. 1, 2015 (Apr. 1, 2015), pp. 106-116, XP055212072.

Kuhn Michael et al: "Time-resolved extraction of caffeine and trigonelline from finely-ground espresso coffee with varying particle sizes and tamping pressures", Journal of Food Engineering, Barking Essex, GB, vol. 206, Mar. 6, 2017 (Mar. 6, 2017), pp. 37-47, XP029969213,ISSN: 0260-8774.

Extended European Search Report for corresponding European patent application No. EP 18 88 6750, dated Jul. 15, 2021.

Kuhn, M. et al., "Time-resolved extraction of caffeine and trigonelline from finely-ground espresso coffee with varying particle sizes and tamping pressures", Journal of Food Engineering, vol. 206, p. 37-47 (2017); http://dx.doi.org/10.1016/j.jfoodeng.2017.03.002.

International Search Report and Written Opinion for corresponding PCT application No. PCT/AU2018/051132, dated Dec. 10, 2018.

Office Action in Japanese Patent Application No. 2020-519792 dated Nov. 1, 2022—see attached translation.

Office Action in Chinese Patent Application No. 201880078276.8 dated Dec. 5, 2022—see attached translation.

Office Action in Japanese Patent Application No. 2020-519792 dated May 9, 2023—see attached translation.

* cited by examiner

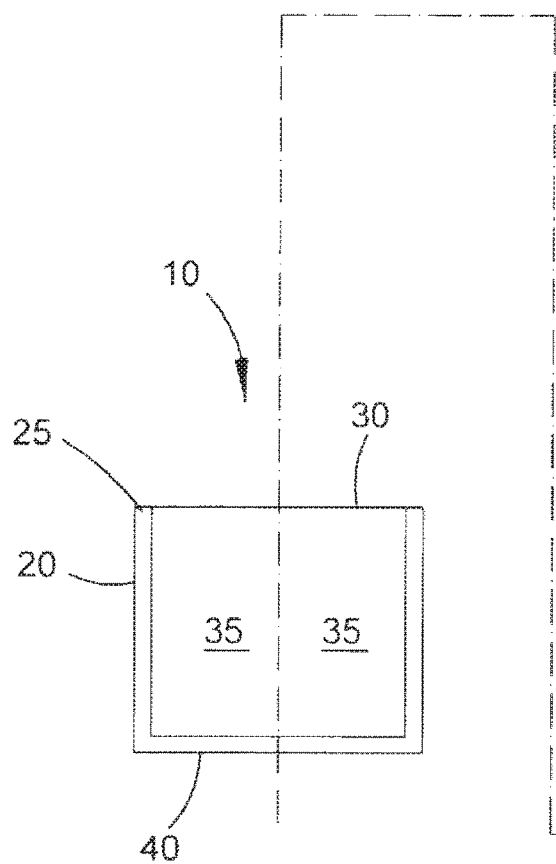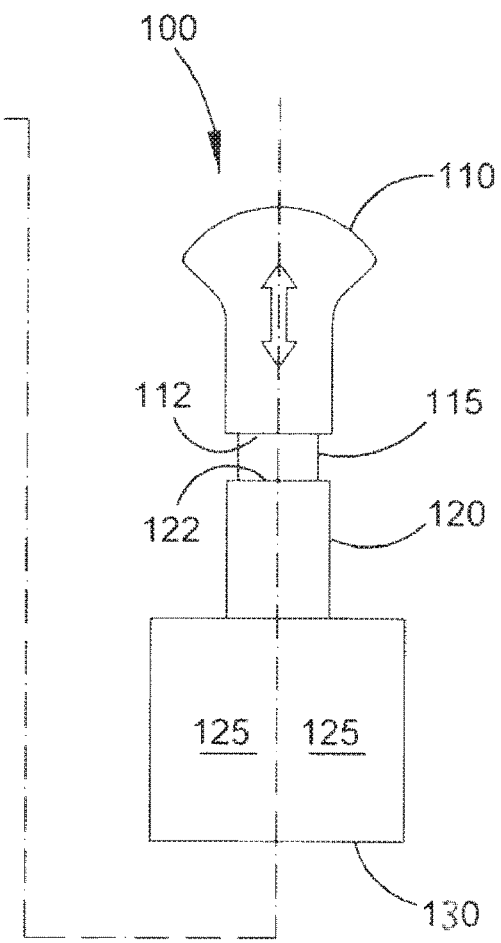
FIG. 1A
FIG. 1B

APPARATUS AND METHODS FOR SETTING A GRIND COARSENESS

FIELD OF THE INVENTION

The present invention is directed generally to the preparation of beverages from ground plant material. In particular, but not exclusively, the invention is directed to defining coarseness of coffee bean grounds in the preparation of a coffee-based beverage.

BACKGROUND TO THE INVENTION

The coffee bean has been used as the basis of a beverage for more than one thousand years, having its origins in North Africa about the $10^{th}$ century. The beverage was introduced to Europeans in the $17^{th}$ century, and today is consumed virtually worldwide and in large quantities.

Coffee beverages can be prepared in many different ways, however all rely on disruption of the physical integrity of the coffee bean, with the extraction of important flavour and bioactive compounds from the interior of the bean into water. Many coffee beverages are produced by firstly roasting the green bean, followed by grinding the bean into a plurality of particles. The particles are contacted with water (typically hot water) such that the coffee compounds are extracted. The solid and liquid phases are separated and the liquid phase consumed.

One example of an extraction method is the well-known espresso extraction process. This process operates by forcing heated water through a prepared bed of coffee particles. The coffee particles are penetrated by the water causing them swell as the sugars and resins within are solubilised allowing them to be carried out of the solid particles by the water. Typically, the ground coffee is placed into a shallow filter basket, and then tamped (compressed) to reduce the volume of the void space between the particles. The reduction in void space volume limits the ability of water to pass through the particle bed unimpeded, and instead forces the water to contact the particles so as to increase the amount of coffee compounds extracted. After tamping, the basket is manually engaged with the espresso machine which pushes heated water through the particle bed, through the filter in the basket, to form a liquor which flows into a coffee cup below.

In a retail environment, coffee beverages are best prepared from whole coffee beans which have been ground immediately before brewing. Control of the grinding conditions is of utmost importance, as incorrect milling can negatively affect the properties of the ground material and therefore, the flavour of the resultant beverage. During grinding, the surface area of the coffee bean material increases, thereby increasing the attack surface area available for the water to contact, which in turn, enables the more efficient transfer of the coffee compounds into the water. In the espresso grind, each single bean is broken into several thousand particles. The grind (i.e. the number and size of the particles into which a bean has been ground) is directly related to the extraction time. The extraction time is the time taken for the water to release the desired contents from the ground particles; with 25 to 30 seconds being considered optimal. Overextraction is to be avoided given the propensity for bitter compounds to be drawn from the bean.

Furthermore, very fine grinds pack together too closely thereby increasing the resistance to water flow through the coffee mass. This resistance can deny water access through the grind during brewing to again affect the taste of the final beverage.

Given the importance of particle size, the prior art provides apparatus and methods for directly or indirectly determining the distribution of particles sizes, and therefore instructs as to the coarseness of fineness of the grind. One commonly used indirect method relies on measuring the length of time taken to perform an extraction of a given volume of coffee liquor. A larger grind size typically results in a shorter time given the larger void volume of a coarse grind. This method is however fraught with unreliability given the potential for extraneous variables such as the tamping force used, basket geometry and the like. Even if all variables are removed, any time period determined as optimum is only relevant to the particular espresso machine, coffee, and the grinder used.

A more direct method of determining particle size is based on a sieving method such as that devised by the United States Department of Commerce in the 1940's. The procedure utilizes a contrivance termed a "RoTap" which consists of four wire screens having decreasing mesh size stacked one on top of the other. When attached to a vibrating machine, coffee particles fall through the various size screens to create a particle distribution. The procedure involves placing a set mass of ground coffee on the uppermost screen and allowing the machine to shake for a set time. Upon completion, all screens are removed and the coffee remaining in each sieve is weighed. By this method a particle distribution curve can be generated.

Whilst the use of a RoTap and similar apparatus allows for a grinding process to be optimised so as to produce a desired particle size distribution, such means are clearly labour and time intensive, wasteful of coffee, and require complex hardware. In any event, unreliable results may be provided, especially at particle sizes preferred for the espresso extraction process (typically a median particle size of around 200 µm).

Given the problems associated with sieving techniques, laser diffraction methods have become widely accepted for the characterization of ground coffee. While these methods provide unprecedented accuracy in the determination of particle size distribution, the instrumentation required is complex, expensive and not suited to use in a retail environment.

While particle size is undoubtedly important, the shape of the particles has a further effect on coffee flavour. Different grinder types (for example, burr versus blade grinders), and different types of grinding surfaces (such as use of a conical burr versus a flat burr) provide a further variable in the general aim of providing a grind which reproducibly provides a superior coffee taste and aroma.

It is an aspect of the present invention to provide improved methods and apparatus for determining an appropriate grind setting for a particular extraction process. In a further aspect, the present invention provides a useful alternative to prior art apparatus and methods.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

After considering this description it will be apparent to one skilled in the art how the invention is implemented in various alternative embodiments and alternative applications. However, although various embodiments of the present invention will be described herein, it is understood that these embodiments are presented by way of example only, and not limitation. As such, this description of various alternative embodiments should not be construed to limit the scope or breadth of the present invention. Furthermore, statements of advantages or other aspects apply to specific exemplary embodiments, and not necessarily to all embodiments covered by the claims.

Throughout the description and the claims of this specification the word "comprise" and variations of the word, such as "comprising" and "comprises" is not intended to exclude other additives, components, integers or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may.

It will be understood that while certain advantages of the invention are described herein it is not represented that all embodiments of the invention will possess all advantages. Some embodiments of the invention may provide no advantage whatsoever and may represent no more than an alternative to the prior art.

In a first aspect, the present invention provides a method for determining at least one characteristic of a mass of particulate plant material, the method comprising the step of determining the density of the mass of particulate plant material.

In one embodiment of the first aspect, the mass of particulate plant material is prepared from a plant seed.

In one embodiment of the first aspect, the mass of particulate plant material is prepared from a coffee bean.

In one embodiment of the first aspect, the mass of particulate plant material is prepared by grinding a plant material.

In one embodiment of the first aspect, the mass of particulate plant material has been compressed. In one embodiment of the first aspect, the particulate plant material has been deliberately compressed.

In one embodiment of the first aspect, the characteristic is the propensity for one or more plant compounds to be water-extracted from the mass of particulate plant seed material.

In one embodiment of the first aspect, the propensity for one or more plant compounds to be water-extracted from the mass of a ground plant seed material is measured by reference to:
  a time taken to extract one or more plant compounds from the mass of particulate plant material, or
  a flow rate of water flowing through the mass of a ground plant material, or
  a time taken to form a given volume of a liquid phase formed from water flowing through the mass, or
  a taste and/or aroma of a liquid phase formed from water flowing through the mass, or an analytical method.

In one embodiment of the first aspect, the characteristic is:
  the surface area of the mass of particulate plant material available for contact with water applied to the mass of particulate plant material, or
  the void volume of the mass of particulate plant material, or
  the gallery size of the mass of particulate plant material.

In one embodiment of the first aspect, the mass of particulate plant material is placed in a vessel, such as an experimental vessel, having a void with one or more dimensions similar or substantially identical to an extraction machine vessel used in the preparation of a liquor produced from the particulate plant material.

In one embodiment of the first aspect, the void is substantially circular in plan view.

In one embodiment of the first aspect, the void is of a diameter similar or substantially identical to an extraction machine vessel used in the preparation of a liquor produced from the particulate plant material.

In one embodiment of the first aspect, the void is of a depth similar or substantially identical to an extraction machine vessel used in the preparation of a liquor produced from the particulate plant material.

In one embodiment of the first aspect, the extraction machine vessel is an espresso basket.

In one embodiment of the first aspect, the level of compression is similar or substantially identical to that applied to a mass of particulate plant material used in the preparation of a liquor produced therefrom.

In one embodiment of the first aspect, the mass of particulate plant material has not been exposed to water.

In one embodiment of the first aspect, the method comprises the steps of:
  measuring the weight of the mass of particulate plant material,
  measuring the volume of the mass of particulate plant material, and
  calculating the density of the mass of particulate plant material.

In a second aspect, the present invention provides a system or apparatus for measuring the density of a mass of particulate plant material, the system or apparatus comprising:
  a vessel having a void configured to retain the mass of particulate plant material therein,
  volume determination means configured to determine the volume occupied by the mass of particulate plant material that has been disposed within the void of the vessel.

In one embodiment of the second aspect, the system or apparatus comprises compression means configured to compress the mass of particulate plant material disposed within the void of the vessel.

In one embodiment of the second aspect, the compression means is configured to substantially evenly compress the mass of particulate plant material disposed within the void of the vessel.

In one embodiment of the second aspect, the compression means comprises a substantially planar compression surface configured to contact the mass of plant material disposed in the void of the experimental vessel.

In one embodiment of the second aspect, the compression means is configured to apply a predetermined compression force to the mass of particulate plant material disposed within the void of the vessel.

In one embodiment of the second aspect, the compression means is configured to be adjustable so as to allow a user-selectable compression force to be applied to the mass of particulate plant material disposed within the void of the vessel.

In one embodiment of the second aspect, the vessel and/or the compression means (where present) is/are configured to allow a user to determine the volume occupied by the mass of particulate plant material that has been compressed within the void of the vessel.

In one embodiment of the second aspect, the vessel or the compression means comprise a user-comprehensible scale configured to allow a user to determine the volume occupied by a compressed mass of the particulate plant material within the void of the vessel.

In one embodiment of the second aspect, the compression means comprises a scale which is readable by reference to an edge or a marking on the vessel.

In one embodiment of the second aspect, the void of the vessel has one or more dimensions similar or substantially identical to an extraction machine vessel used in the preparation of a liquor produced from the particulate plant material.

In one embodiment of the second aspect, the void is substantially circular in plan view.

In one embodiment of the second aspect, the void is of a diameter similar or substantially identical to an extraction machine vessel used in the preparation of a liquor produced from the particulate plant material.

In one embodiment of the second aspect, the void has a depth at least that of the extraction machine vessel used in the preparation of a liquor produced from a particulate plant material.

In one embodiment of the second aspect, the particulate plant material is prepared from a plant seed.

In one embodiment of the second aspect, the particulate plant material is prepared from a coffee bean.

In one embodiment of the second aspect, the system or apparatus comprises weighing means configured to weigh the mass of particulate plant material disposed in the vessel.

In one embodiment of the second aspect, the weighing means is a balance having a tare function.

In one embodiment of the second aspect, the system or apparatus comprises density calculation means configured to accept as input (i) volume data as provided by the volume determination means, and (ii) weight data as provided by the weighing means; and to provide as output (iii) a density calculated from the volume data and the weight data.

In one embodiment of the second aspect, the density calculation means is embodied in application software executable on a processor-enabled device.

In one embodiment of the second aspect, the processor-enabled device is a mobile device.

In a third aspect, the present invention provides a method for determining the density of a mass of particulate plant material, the method comprising the steps of
 measuring the weight of the mass of particulate plant material,
 measuring the volume of the mass of particulate plant material, and
 calculating the density of the mass of particulate plant material.

In one embodiment of the third aspect, the method comprises the step of placing an amount of particulate plant material into the void of the vessel as defined in applicable embodiments of the second aspect.

In one embodiment of the third aspect, the method comprises the step of compressing the mass of particulate plant material before measuring the volume of the plant material.

In one embodiment of the third aspect, the step of compressing is performed using the compression means as defined in any applicable embodiment of the second aspect.

In one embodiment of the third aspect, the step of measuring the density is performed using the apparatus or system of the second aspect.

In one embodiment of the third aspect, the step of weighing is performed using the weighing means as defined in any applicable embodiment of the second aspect.

In one embodiment of the third aspect, the step of calculating is performed using the density calculation means as defined in any applicable embodiment of the second aspect.

In a fourth aspect, the present invention provides a method for setting a plant material grinder with respect to coarseness or fineness of the resultant grind, the method comprising the steps of:
 providing a plant material,
 grinding the plant material using a grind setting so as to provide a test batch of particulate plant material,
 assessing the density of the test batch of particulate plant material by the system or apparatus of any embodiment of the second aspect, or by the method of any embodiment of the third aspect, and
 adjusting the grinder setting if necessary so as to provide a target density for the particulate plant material.

In one embodiment of the fourth aspect, the grinder is a coffee bean grinder of the type used in a retail or a domestic environment.

BRIEF DESCRIPTION OF THE DRAWINGS

FIG. 1A is a diagrammatic cross-sectional lateral view of a preferred vessel of the present invention.

FIG. 1B is a diagrammatic lateral view of a preferred compression means of the present invention suitable for use with the vessel of FIG. 1A.

DETAILED DESCRIPTION OF THE INVENTION

Figure 2A:
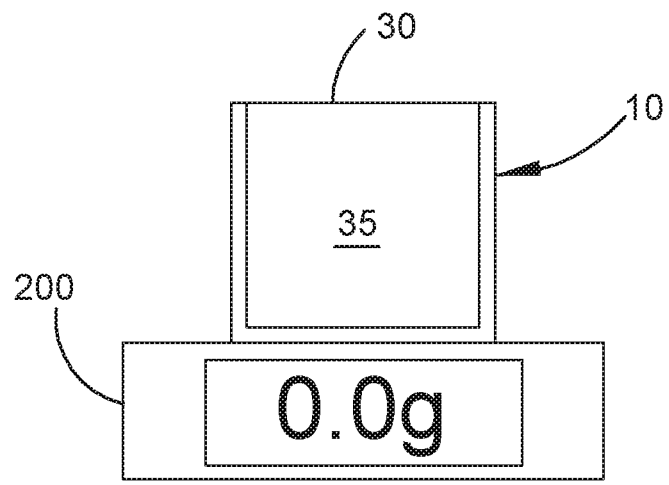
FIGS. 2A, 2B, 2C, and 2E show preferred method steps used in conjunction with the vessel of FIG. 1A and the compression means of FIG. 1B to determine the density of an amount of ground coffee.

The present invention is described herein mainly by reference to ground coffee beans as the mass of particulate coffee beans, and particularly with regard to the use of ground coffee beans in an espresso extraction method. This is for the sake of clarity and brevity, and should not be taken as any restriction on the ambit of the present invention.

The present invention is predicated at least in part on the Applicant's finding that characteristics of ground coffee may be better considered where the mass of ground coffee is considered as a whole by way of density measurement. This is in contrast to prior art methods which rely on the measurement of the sizes of individual coffee bean particles to generate a particle size distribution curve. Even where the present invention does not provide any advantage in terms of superior characterisation of the ground coffee, advantage may be provided in that the present methods, apparatus and systems are more simple or economical as compared with the prior art.

Accordingly, in a first aspect the present invention provides a method for determining at least one characteristic of a mass of particulate plant material, the method comprising the step of determining the density of the mass of particulate plant material. As applied to the espresso extraction of ground coffee beans at least, the skilled person is entirely familiar with the various means by which coffee beans (which are in fact seeds of the coffee plant) may be roasted and ground for use in the preparation a coffee liquor for consumption. The skilled person understands that the ground coffee may be placed in a filter basket and compressed to some degree with a tamp or similar contrivance in preparation for heated water from the coffee machine to be forced through the compressed ground coffee mass so as to form a liquor. These well-known means of preparing a liquor are utilized in the context of the present invention given the general aim of reproducing so far as possible the conditions under which ground coffee is prepared. Given that the present invention in the first aspect is directed to methods for determining at least one characteristic of a ground coffee bean mass, the characteristics so determined should be reflective of and relevant to methods used in the real world to prepare coffee. In this way, any characteristic so determined by the method may be applied to the actual production of a coffee liquor for consumption using a retail or a domestic coffee machine.

As will become clear from considering this specification in its entirety, preferred forms of the invention require various items of hardware that mimic those used in the retail and domestic preparation of coffee beverages. Furthermore, various method steps are configured to mirror the actions of a person preparing coffee beverage.

As is clear form the Background section, the coffee liquor is the liquid phase resulting from the water extraction of desirable (and sometimes undesirable) compounds from the ground coffee bean. It is proposed that determination of the density of the whole ground coffee mass provides an indication of the propensity for the coffee compounds to be water-extracted from the mass of particulate plant seed material. This propensity for extraction is applicable to both desirable and undesirable coffee compounds, and is therefore key in setting a grind (with respect to coarseness or fineness) to extract the desirable compounds while leaving the undesirable compounds in the bean material. As the skilled person understands, undesirable compounds are typically extracted later in the brewing process, and so a grind coarseness or fineness is chosen so as favour the extraction of desirable components over undesirable components for a given extraction time (normally 25 to 30 seconds). Where the propensity for water extraction is higher, a coarser grind may be used so as to inhibit the extraction of undesirable compounds within the extraction time. In a coarser grind, the particles of coffee bean have a relatively low surface area to volume ratio, and accordingly compounds are less rapidly extracted. This delays the extraction of undesirable compounds and therefore provides a greater likelihood that such compounds do not enter the liquor. A negative corollary is that desirable compounds may be extracted in lower amounts.

Conversely, in a finer grind the particles of coffee bean are smaller and have a relatively high surface area to volume ratio, and accordingly compounds are more rapidly extracted. This increases the extraction of desirable compounds and therefore provides a greater likelihood that such compounds enter the liquor. A negative corollary is that undesirable compounds may be extracted in higher amounts.

Thus, a balance must be arrived at in order to provide a coffee liquor with a full flavour, but with limited amounts of bitter undesirable compounds.

As provided by the present invention, a person seeking to prepare a coffee liquor in a manner that favours the extraction of desirable over undesirable compounds may refer to a target density of the coffee to decide an appropriate coarseness or fineness setting on a coffee bean grinder.

Other parameters such as the force of compaction of the coffee particles, or the mass of coffee particles, or the extraction time, or the water temperature or the water pressure may be modified so as to achieve the general aim of favouring the extraction of desirable over undesirable compounds, however setting of the grinder is preferred for reasons of simplicity and reproducibility.

The propensity for a plant compound to be water-extracted from the ground coffee bean mass may be measured by reference to: the time taken to extract one or more plant compounds (a shorter time being indicative of a higher propensity), or a flow rate of water flowing through the mass (a longer time being indicative of a higher propensity), or a time taken to form a given volume of a liquid phase (a longer time being indicative of a higher propensity), or a taste and/or aroma of a liquid phase formed from water flowing through the mass (a stronger flavour or aroma being indicative of a higher propensity). A highly subjective method for determining the propensity for a plant compound to be water-extracted from the ground coffee bean mass is by use of analytical techniques. Tools such as spectrophotometry, mass spectrometry, chromatography (such as TLC or GC) and the like may be used to identify and quantitate water-extracted coffee compounds.

The density of a coffee ground mass may also reflect characteristics of the spaces (or "galleries") between the coffee bean particles. Together, the spaces form the "void volume" of the coffee bean particle mass. These spaces affect how the water passes through the mass. Where the spaces are small, water must take a more tortuous path from the water entry point (typically the upper face of the mass) to the water exit point, typically the bottom face of the mass. A more tortuous path will generally increase the water residence time in the mass, thereby increasing the opportunity for coffee compounds to be extracted.

Measuring the density of the coffee ground mass may be achieved by any means deemed suitable by the skilled artisan. As is well known in the art, density is calculated by reference to a weight per unit volume. For example, 1 g of water has a volume of 1 $cm^3$. Accordingly, the density of water may be expressed as 1 $g/cm^3$.

As will be appreciated, means for density determination that is cost-effective and easy to implement in a retail or a domestic environment is preferred.

In one aspect of the invention there is provided a system or an apparatus for measuring the density of a mass of particulate plant material, the system or apparatus comprising: a vessel having a void configured to retain the mass of particulate plant material therein, volume measurement means configured to measure the volume occupied by the mass of particulate plant material that has been disposed within the void of the vessel. This aspect of the invention may be provided by way of a substantially unitary apparatus having a number of components that function in a cooperating manner. Alternatively the components may be discrete yet nevertheless form a system, in which case the components may be operated substantially independently.

In order to faithfully reproduce the density of the coffee particles as would be observed when used in an actual beverage making process, the vessel is preferably configured to reproduce the vessel in which the ground coffee mass is disposed in the context of an extraction machine (in this case, a coffee making machine capable of causing water, preferably heated water, through the coffee particle mass with or without the assistance of pressure). The vessel typically comprises a void to receive the ground coffee. The void is generally of fixed internal dimension, with at least one dimension being consistent with a dimension of an extraction machine vessel. Where the void is cylindrical (which is typical for filter baskets) the diameter of void is consistent with that of the filter basket of the extraction machine which is intended to produce the actual coffee liquor for consumption. The diameter of the experimental vessel void may be about 50 mm, 51 mm, 52 mm, 53 mm, 54 mm, 55 mm, 56 mm, 57 mm, 58 mm, 59 mm or 60 mm. Preferably the diameter is about 53 mm or 58 mm, and is more preferably 58 mm in diameter. Where the void has two or more diameters, any of the aforementioned diameters may be the greatest of the diameters, or the diameter in an uppermost region of the vessel.

The void may be formed so as to have a profile similar to or substantially the same as that of the filter basket for which it is intended to replicate. In some embodiments, there is a lower region of the void which is of smaller diameter than the upper region so as to mimic a particular type of filter basket that is often used in the making of coffee beverages.

The depth of the vessel will suitably be at least the depth of the coffee machine filter basket used to prepare the coffee liquor for consumption. Typically the void will be somewhat deeper given the need to insert a tamp, and in some embodiments the tamp being required to be disposed some way down inside the void such that a measurement may be read from a scale engraved on the tamp against the vessel upper edge, as further described infra.

The vessel is typically fabricated from a rigid and deformation-resistant material such as a high impact plastic, or a metal such as stainless steel. In some embodiments, a tamp is used to compress the coffee particle mass and the void should maintain its geometry and dimensions in the face of forces exerted.

In some embodiments, the vessel has an upwardly extending wall capable of (i) retaining uncompressed coffee particles before tamping, and (ii) guide a compression means downwardly and onto the coffee particles to mimic the tamping process. The sidewall may serve the further function of ensuring that the lower surface of the compression means is maintained parallel to the floor of the vessel so as to ensure the coffee is compressed evenly.

The present apparatus or system may comprise compression means, typically in the form of piston-like contrivance having a planar lower face configured to contact and bear against the coffee particles in the upper region of the mass. The compression means is typically configured to fit snugly within the void of the vessel, and be capable of sliding upwardly and downwardly therein in a piston-like manner. The compression means is generally used to mimic the process of tamping the coffee particles into a compressed form, as is performed normally in the espresso extraction process.

At the end opposing the planar lower surface is typically a handle of some description configured to allow a user to exert a downward force thereon, and also to remove the compression means from the void. The planar face and handle are typically connected by a member, stem or other suitable structure.

The compression means may comprise a mechanism allowing for a predetermined force to be applied to the coffee particles disposed within the void. This allows for replication of the tamping process, whereby a force of about 10 kg, 15 kg or 20 kg is applied by a user to the tamp handle.

For example, the compression means may comprise a spring which when compressed a predetermined distance exerts the predetermined force. In this embodiment, the spring is connected to the compression means handle at one end and a head region having the planar face at the other end. Thus, the handle can be pushed downwardly until the lower edge of the handle contacts a ledge on the head region. At that juncture, the predetermined force has been applied to the coffee particles, and the user permitted to release the handle and allow the spring to recoil.

In order to calculate density, the volume of the compressed coffee particle mass is measured. In one embodiment of the system or apparatus, the vessel or compression means has a scale applied thereto. In one embodiment, the vessel may be transparent and the upper edge of the compressed coffee particle mass readable against a scale printed onto the vessel wall in much the same way the volume of a fluid in a burette is read against a scale. Where the vessel is opaque, the compression means may have a scale along its length. The scale may be read against the top edge of the vessel so as to provide an indication of the depth of the compressed coffee particle mass. The scale is read with the planar face of the compression means resting on the upper surface of the compressed coffee particle mass. The more shallow the depth of the compressed particle mass, the deeper the compression means is allowed to sit within the void, and the lower the number read off the scale on the compression means. As will be appreciated, the scale will therefore be gradated with higher numbers toward the lower end of the scale (i.e. the end of the scale more proximal to the planar surface) and lower number toward the upper end of the scale (i.e. the end more proximal to the handle of the compression means). To improve accuracy, the scale may be configured as a Vernier scale or similar.

The depth of the compressed coffee particle mass is recorded for use in the calculation of density.

Also required for the density calculation is the weight of coffee used to form the coffee particle mass. Typically, a weight is used which is consistent with the actual espresso extraction process to be mimicked. The weight may be about 10 g, 11 g, 12 g, 13 g, 14 g, 15 g, 16 g, 17 g, 18 g, 19 g, 20 g, 21 g, 22 g, 23 g, 24 g, 25 g, 26 g, 27 g, 28 g, 29 g, or 30 g. Weights in the range of about 15 g to about 25 g are commonly used in the preparation of a coffee liquor.

The coffee may be weighed in a separate vessel and then transferred to the vessel. More conveniently the coffee is weighed in situ by firstly placing the vessel on the platform of a weighing means (such as a balance), and then taring the balance to zero. Coffee particles are then added to the vessel while the user reads the balance until the required weight is reached.

The present invention may be extended further to characterization of plant material (and preferably coffee beans) higher in the supply chain. For example, the vessel of the present invention may be used to measure density of green and roasted beans. Green bean is traditionally traded from green bean merchants with a bulk density reading, usually expressed in hectolitres (1 hectolitre=100 litres). It is done this way to indicate how dense the bean is as part of the product sheet. This and other information on the sheet helps the coffee bean roaster to determine roasting profiles. The denser the bean, the higher the hectolitre reading, and usually the more heat required to roast it.

Bulk Density Verses Density

The Applicant proposes that a bulk density measurement performed according to the prior art is inherently flawed. Bulk density is a collection of beans, i.e. a "bulk amount" of beans which is inclusive of air voids in the total measurement. These air spaces can provide errors in calculation given that they are included in the total volume used to calculate density, but have a density of essentially zero. Larger or smaller beans have size different sized air spaces which in turn will give different density readings based on the differential volumes of the void airspaces. Smaller airspaces will naturally provide more beans per volume and therefore give the indication of a denser bulk density, when in fact it may not be the case. It has been found that a more accurate bean density reading may be provided by taking account of the void spaces between beans. Reference is made to Example 2 herein detailing a method of calculating true bean density using water to calculate the void volume of the airspaces present between the bean and then to calculate a bean density in a manner that discounts the confounding effect of void airspaces.

Not only does using the bush and bush density cup hold the advantage of determining density of both green and the resulting roasted bean, but in conjunction with a moisture meter readings and roasted weight loss information allow for roasting profiles to be customized to achieve a resulting brew profile which may be accurately duplicated across various bean densities.

Green been to Roasted Bean to Brewed Coffee Beverage.

Because the Bush and Bush density cup is already used to create specific density readings for espresso coffee, the present invention provides means to generate roast and brew profiles covering the entire span from green bean, to roasted bean, to ground bean, by using accurately determined whole bean density and ground bean density as a means for characterizing coffee in a cohesive manner from the green bean state used for roasting, through to the ground state used for brewing coffee beverages. Accordingly, in one aspect the present invention provides a method for characterizing a plant bean material comprising the steps of (i) measuring the density of the beans of the plant bean material in a manner which discounts the presence of airspaces about the beans, and (ii) measuring the density of ground material prepared from the plant bean material. Preferably the step of measuring at step (i) is by a method as described herein. Preferably the step of measuring at step (ii) is by a method as described herein.

Reference is now made to FIG. 1A shows an exemplary experimental vessel, and FIG. 1B which shows a compression means suitable for use with the vessel.

Turning firstly to the experimental vessel 10, the vessel is generally cup-shaped having a cylindrical wall 20 defining an upper edge 25 which is circumferential to an opening 30. A large cylindrical void 35 is defined by the wall 20 and floor 40.

The compression means matched to the vessel in this embodiment is a modified tamp 100, having a handle 110, with a handle member 115 slidingly engaged with a sleeve 120, the sleeve 120 in turn is attached to the head 125. The head 125 terminates in a planar surface 130.

The 110 handle and handle member 115 (being fixed together) are movable upwardly and downwardly by a user. The handle 110 and handle member 115 are biased in the upward direction (as drawn) by an internal spring (not shown). When the handle 110 is urged downwardly by the user, the downward force is transferred to the internal spring, and in turn from the spring to head 125. The handle 110 is urged downwardly only to the point that the lower edge 112 of the handle 110 collides with the upper edge 122 of the sleeve 120. At that point, a predetermined force is applied to the head 125. In one embodiment, the tamp mechanism can be provided with an internal spacer (not shown) which cooperates with the spring. The spacer can be changed with a different spacer to provide different tamp pressures to simulate the different pressures that may be used in the industry for the preparation of a liquor such as coffee and allow the user to set the tamp at a particular tamping pressure. In another embodiment, to minimise measurement inaccuracies, a set spring is used and the tamp is calibrated to a specific pressure (suitably 15 Kg).

The method of use of the vessel 10 and tamp 100 to determine the density of an amount of coffee particles now follows.

Example 1: Method for the Determination of the Density of a Coffee Bean Grind

This exemplary method requires the experimental vessel 10 as shown in FIG. 1A, and the matched tamp 100 as shown in FIG. 1B.

Step 1: The vessel 10 is placed on a balance 200, and the balance 200 tared to zero, as shown in FIG. 2A.

Figure 2B:
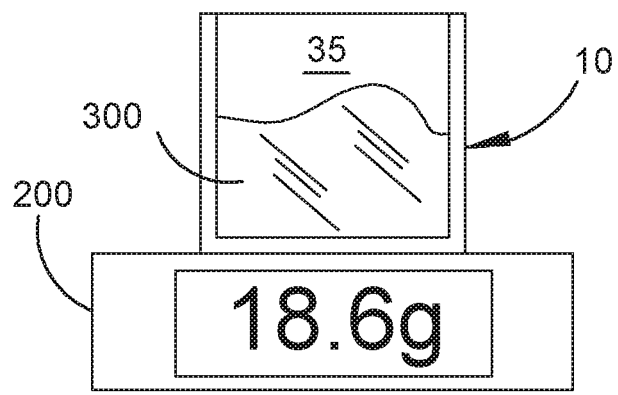

Step 2: The vessel 10 is loaded with an amount of ground coffee 300 which would typically be used in a filter basket extraction. The weight of ground coffee is noted (in this example, 18.6 g), and entered into the density calculation application software. Reference is made to FIG. 2B.

Figure 2C:
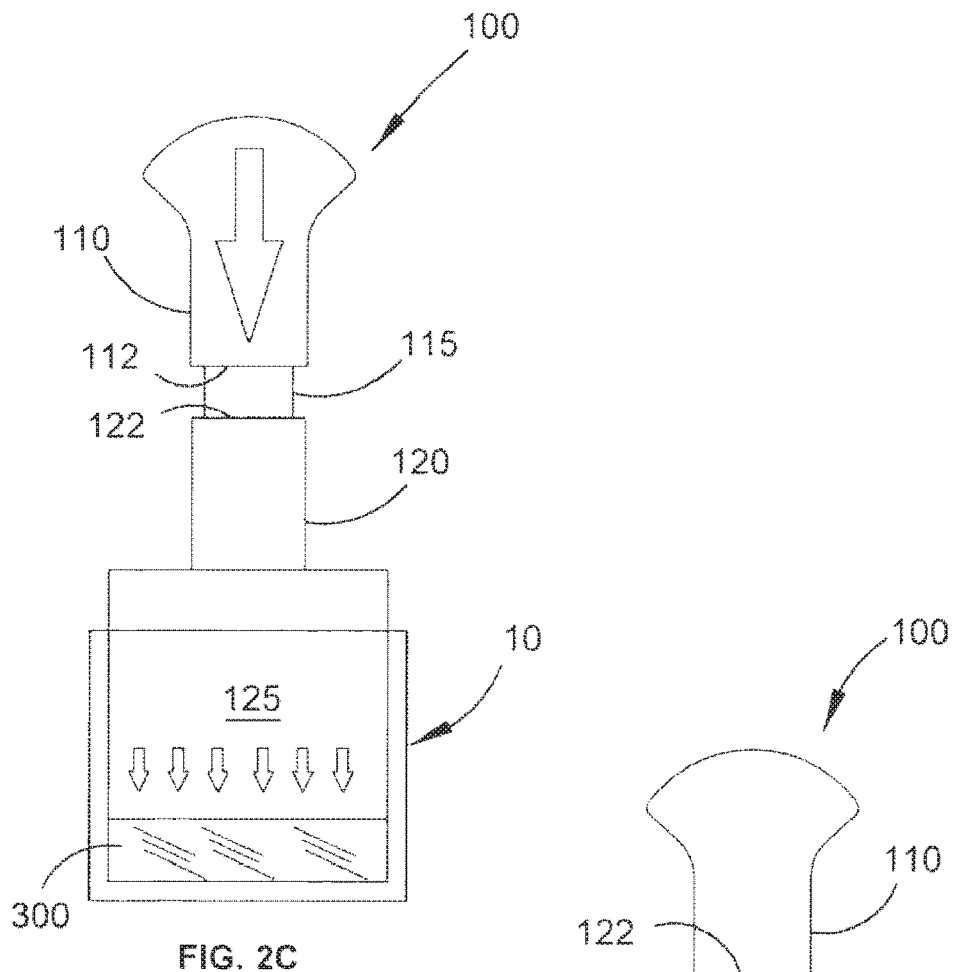

Step 3: The vessel 10 is removed from the balance 200 and placed on a firm surface and gently oscillated in a side-to-side-manner so as to gently level the contained grounds. The tamp head 125 is inserted into the vessel void 30, as shown in FIG. 2C.

Figure 2D:
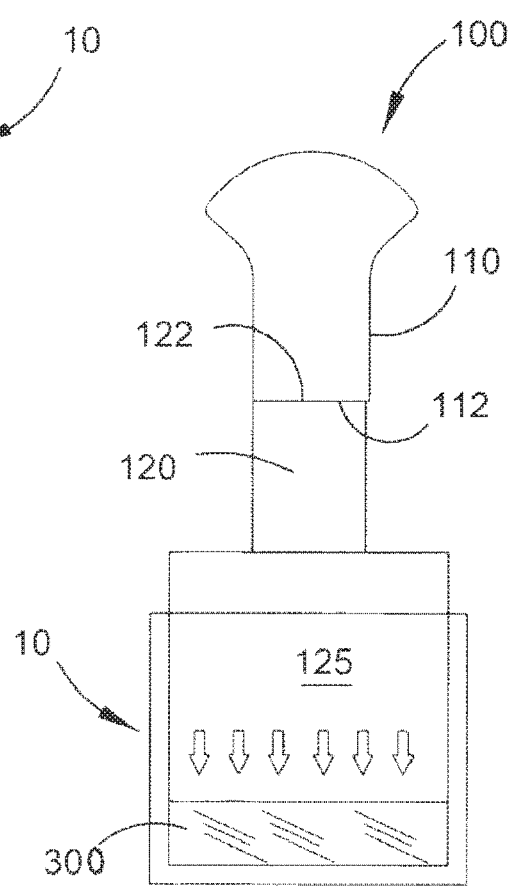

Step 4: The tamp handle 110 is pushed down until the lower edge 112 of the handle 110 just touches the upper edge 122 of the sleeve 120, as shown in FIG. 2D. This indicates that a predetermined compression force has been applied to the ground coffee (the downward force indicted by the small arrows). The tamp 100 can be adjusted to exert a force of 10 kg, 15 kg or 20 kg. Industry standard is typically 15 kg, and in this example a tamp force value of 15 kg was used.

Figure 2E:
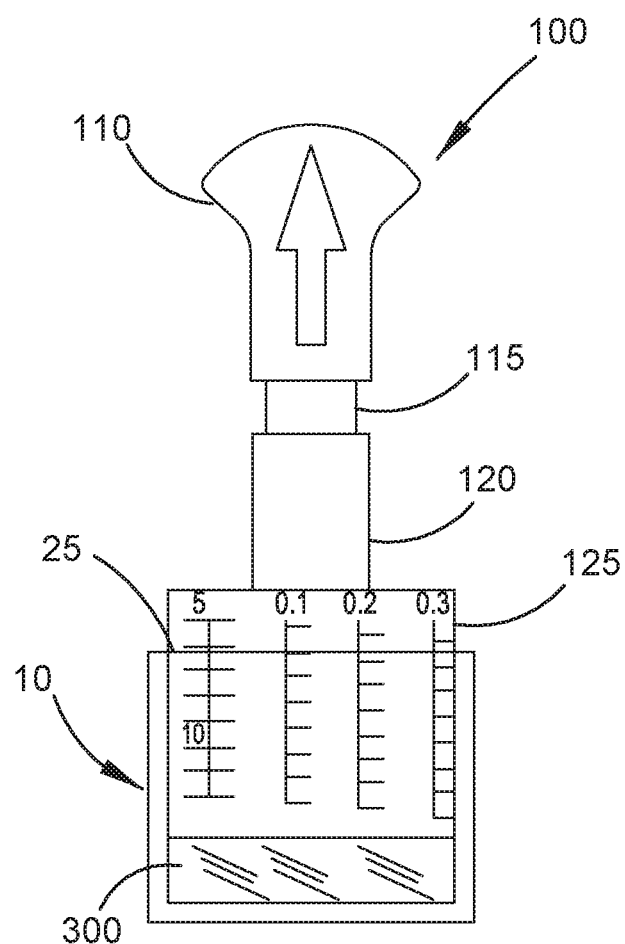

Step 5: The tamp handle 110 is released, and the scale marked on the outside of the tamp head 125 is read against the top edge 25 of the vessel 10, as shown in FIG. 2E. Firstly, the user reads the whole numbers scale, i.e. the whole number above the top edge, and then the $\frac{1}{10}$th unit that is positioned level with the top edge. In this example the measurement would be 6.1 mm. This is tamp length value, and is entered into the application software. As shown in the drawing, the scale includes whole numbers from 5 to 12 mm (with 5 mm and 10 mm displayed), $\frac{1}{10}^{th}$ units (i.e., 0.1 mm), $\frac{1}{20}^{th}$ units (i.e., 0.2 mm) and $\frac{1}{30}^{th}$ units (i.e., 0.3 mm). In one embodiment $\frac{1}{40}^{th}$ units (i.e., 0.4 mm) may be displayed. In practice, the whole number scale may be 5 to 35, with 5, 10, 15, 20, 25, 30 and 35 numbers displayed. In one embodiment the whole numbers 5, 10, 15, 20 and 25 are displayed. In addition, in one embodiment only the $\frac{1}{10}$ unit and/or $\frac{1}{20}^{th}$ units are shown.

The Volumetric Density Formula D=M/V can now be satisfied (by software means) according to the equation:

$$D=M/(\pi r^2 \times TL)$$

Where:
- D is the density of the compressed ground coffee particles (at the tamp force used),
- M is the mass of ground coffee that was used for the test (in grams),
- r is the radius of the vessel void (in mm), and
- TL is the tamp length value read from the engraved scale after compression with the tamp at 15 kg.

In this example, the aim was to reproduce conditions for a standard 58 mm filter basket, and so a vessel having a void diameter of 58 mm (radius of 29 mm) was used.

D is therefore solved for as follows:

$$D = 18.6 \text{ g}/(\pi \times 29 \text{ mm}^2 \times 6.1 \text{ mm}) \ast 0.001$$

$$D = 18.6 \text{ g}/16.1136$$

$$D = 1.154$$

Figure 3A:
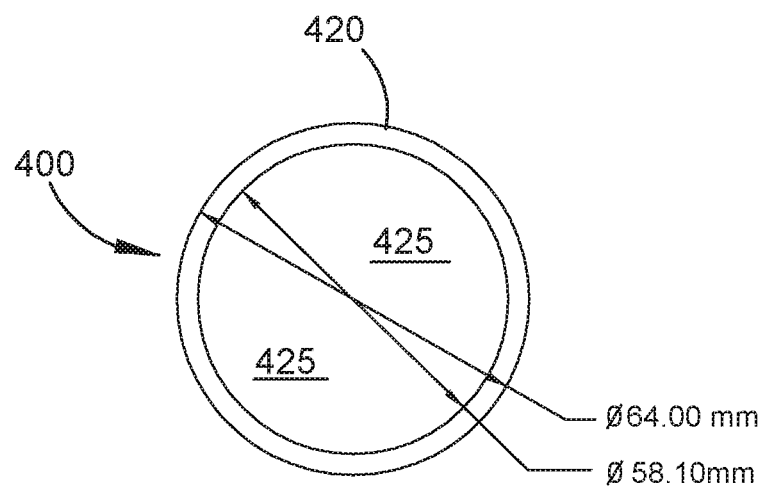
FIG. 3A is a plan view of an exemplary vessel. The dimensions shown are exemplary only, and not limiting on the invention.
Figure 3B:
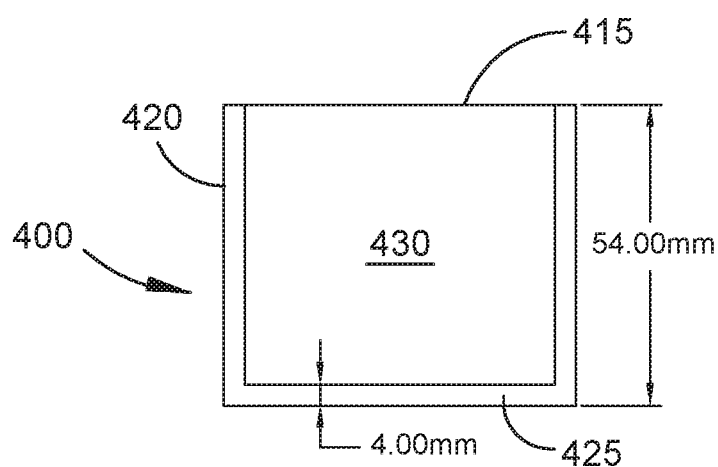
FIG. 3B is a diagrammatic cross-sectional lateral view of the vessel of FIG. 3A. The dimensions shown are exemplary only, and not limiting on the invention.

Reference is now made to FIG. 3A and FIG. 3B which show in isolation an exemplary experimental vessel 400, being generally cylindrical and having an opening 415 defined by a wall 420. A void 430 is defined by the wall 420 and floor 425. The vessel 400 is milled from solid stainless steel.

Example 2: Method for the Determination of Coffee Bean Density

This exemplary method requires the experimental vessel 10 as shown in FIG. 1A, and a screen which fits within the vessel.

Step 1: An empty experimental vessel with screen is placed on balance which is then tared to zero Step 2: The screen is removed and the experimental vessel is filled with beans, and the screen disposed on top of the beans. The weight of the beans is noted. In this example the weight is 83.3 g.

Step 4: The experimental vessel is filled to the brim with water. The weight of the beans plus the water is recorded. In this example, the weight is 144.7 g.

Step 5: Using the following Formula the density of the whole beans (which may be green or roasted) is calculated.
- BD is Bean Density
- BW is Bean Weight
- WW is Wet Weight
- Vessel volume is 131

$$BD = BW/(131 - (WW - BW))$$
$$= 83.3/(131 - (144.7 - 83.3))$$
$$= 83.3/(131 - 61.4)$$
$$= 83.3/69.6$$
$$= 1.19$$

Figure 4:
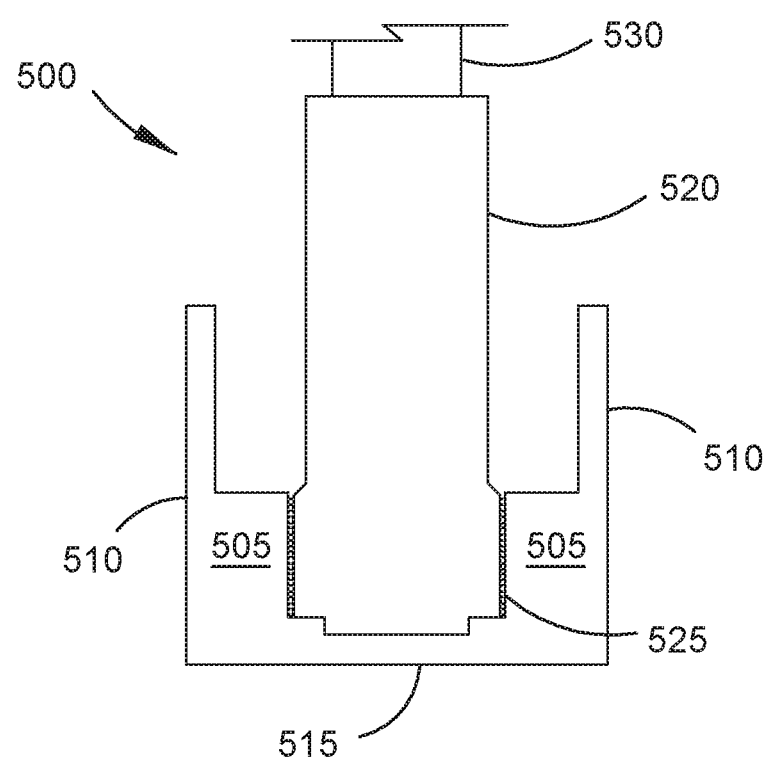
FIG. 4 is a diagrammatic cross-sectional lateral view of an exemplary tamping device of the present invention, configured to be used with the vessel of FIGS. 3A and 3B.

Reference is now made to FIG. 4 which shows an exemplary tamp, configured to snugly fit within the cylindrical void 430 of the experimental vessel 400 shown in FIG. 3B. The tamp 500 has a cylindrical head 505 milled from solid stainless steel, and having a smooth external wall 510 and a lower tamping surface 515 which contacts coffee grounds contained in the experimental vessel 400. In use, the external wall 510 of the head 505 sliding engages with the internal wall of void 430 of the experimental vessel 400 of FIG. 3B so as to ensure that the tamping surface 515 remains parallel with the vessel 400 floor 425, which in turn ensures even tamping of the coffee grounds. The tamp 500 has a cylindrical stem 520 which screws firmly into a thread 525 of the head 505. The stem 520 has axial cylindrical lumen into which a handle member 530 extends. The handle member 530 slidingly engages and moves coaxially within the stem 520 lumen. The handle member 530 when in the most downward position (as occurs when pushed downwardly by a user) exerts a tamping pressure (by way of surface 515) on the coffee grounds below.

A mechanism may be incorporated into the tamp 500 to ensure that a predetermined maximum tamping pressure is applied by way of surface 515 on the coffee grounds below. For example, the mechanism may involve a spring connection which connects the handle member 520 and cylindrical stem 530, and restricts the maximum pressure that can be applied by the user pushing downwardly. In certain embodiments, the mechanism is adjustable to allow the user to select a predetermined maximum tamping pressure. Of course, the present invention is not restricted to any particular mechanism.

Given the benefit of the present specification, the skilled artisan will be enabled to design vessels to mimic vessels used in the production of a beverage or indeed any other liquid phase derived from the extraction of a plant material. The skilled artisan will be further enabled to design tamps matched to any such vessel.

Example 3: Using the Apparatus of the Invention to Set a Plant Material Grinder with Respect to Coarseness or Fineness of the Resultant Grind Each coffee grinder manufacturer has their own markings on their grinders to provide an indication on where to set a grind. These markings (typically numbers and/or words such as course/fine) are usually placed circularly around the collar of a grinder plate, the underside of which holds a top stationary burr. The markings represent a "ballpark" grind size and cannot be used as an exact reference tool by baristas because the markings on grinders between different manufacturers vary greatly depending on collar size and the screw pitch plate used. The markings indicate the direction of the pitch thread. By moving the collar towards a course marking, the burrs are moved further apart by opening the top burr plate and the particle size of the resulting ground material will be greater. Conversely, by moving the collar towards an opposite or finer marking, the burr plates are moved closer together and the particle size of the resulting ground material will be smaller. In use, the smaller particle size of the finer ground material presents a greater surface area resulting in greater extraction and a stronger coffee.

For a particular grinder, a barista may make a mark on the collar (and even on the body of the grinder) to indicate the point where the resulting grind has the desired particle size for extraction of a particular coffee strength and quality and place additional marks where the grind is too coarse of too fine. Unfortunately, whilst these markings can be used as a guide, the point where the resulting grind has the desired particle size for extraction will continue to change, for example, with the coffee used, blade wear, collar size, pitch plate used, weather conditions and friction, which all create variables to particle mass and volume. The marking is only relevant to the coffee in the grinder at that time (and would differ depending on the density of the coffee). Also the marking is only for the particular grinder used and cannot be transferred to another grinder. A barista may need to make minor adjustments of the applied marks several times a day in order to ensure the desired particle size for extraction. In this case, the marks may be adjusted by as little as a few millimetres.

By use of the apparatus of the invention, it is possible to set a coffee grinder with respect to coarseness or fineness of the resultant grind based on a target density. 20 grams of various grinds of coffee beans were separately placed into an experimental vessel of FIG. 1A and tamped to a specified pressure. The volume was then recorded using the volume scale provided on the apparatus and the density then calculated.

The results were as follows:

| Grind | Volume | Density |
| --- | --- | --- |
| Too fine | 13.5 mm | 0.560 |
| Desirable Grind | 13.9 mm | 0.544 |
| Too Course | 14.3 mm | 0.529 |

It is clear from this table that as the grind gets course the density decreases. The apparatus of the invention can provide a target density for grinding a particular batch of coffee. The target density value can then be used by a different barista (including one of lesser skill) to set a grind for the batch of coffee.

The method using the apparatus of the invention can be duplicated across grinders and there is no longer any need for a barista to include their own grinder markings. The density reading can also be used for coffee testing, to check for burr wear, geometry and to provide a valuable standardised measurement system to calibrate from roasted bean density to coffee extraction.

It will be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. Functionality may be added or deleted from diagrams and operations may be interchanged among functional blocks. Steps may be added or deleted to methods described within the scope of the present invention.

We claim:

1. An apparatus for measuring the density of a test batch of a mass of particulate plant material prior to placing the mass of particulate plant material in an extraction machine, the apparatus comprising:
    a vessel having a void configured to retain a weighed or weighable mass of the test batch of particulate plant material therein,
    volume determination means configured to determine the volume occupied by the test batch of particulate plant material that has been disposed within the void of the vessel; and
    a compression means configured to compress the test batch of mass of particulate plant material disposed within the void of the vessel;
    wherein the density of the test batch is calculable from a weighed mass per unit volume of the test batch of the particulate plant material.

2. The apparatus of claim 1, wherein the compression means
    is configured to substantially evenly compress the mass of particulate plant material disposed within the void of the vessel or is configured to apply a predetermined compression force to the mass of particulate plant material disposed within the void of the vessel.

3. The apparatus of claim 1, wherein the compression means comprises a substantially planar compression surface configured to contact the mass of plant material disposed in the void of the vessel.

4. The apparatus of claim 1, wherein the vessel and/or the compression means is/are configured to allow a user to determine the volume occupied by the mass of particulate plant material that has been compressed within the void of the vessel.

5. The apparatus of claim 1, wherein the void of the vessel has one or more dimensions similar or substantially identical to an extraction machine vessel used in a preparation of a liquor produced from the particulate plant material.

6. The apparatus of claim 1, wherein the particulate plant material is prepared from a plant seed or from a coffee bean.

7. The apparatus of claim 1, wherein the vessel replicates an espresso filter basket of the extraction machine.

8. The apparatus of claim 1, comprising one or more of
    (i) weighing means configured to weigh the mass of particulate plant material disposed in the vessel;
    (ii) density calculation means configured to accept as input (i) volume data as provided by the volume determination means, and (ii) weight data as provided by the weighing means, and to provide as output;
    (iii) a density calculated from the volume data and the weight data.

9. The apparatus of claim 1 wherein the mass of particulate plant material is prepared by grinding a plant material.

10. The apparatus of claim 1 when used to determine the density of a mass of particulate plant material.

11. The apparatus of claim 10, wherein a level of compression when used is similar to or substantially identical to that applied to a mass of particulate plant material used in a preparation of a liquor produced therefrom.

12. A method for determining the density of a test batch of a mass of particulate plant material prior to placing the mass of particulate plant material in an extraction machine, the method comprising the steps of:
    placing the test batch of the mass of particulate plant material into the void of the vessel as defined in claim 1, measuring the weight of the test batch of the mass of particulate plant material, measuring the volume of the test batch of the mass of particulate plant material, and calculating the density of the mass of particulate plant material, by dividing the weight of the weighed mass of the test batch of the mass of particulate plant material by the volume of the test batch of the mass of particulate plant material.

13. The method of claim 12, comprising the step of compressing the mass of particulate plant material using the compression means before measuring the volume of the plant material.

14. A method for setting a plant material grinder external to an extraction machine with respect to coarseness or fineness of the resultant grind, the method comprising the steps of:

providing a plant material, grinding the plant material using a grind setting so as to provide a test batch of particulate plant material, assessing the density of the test batch of particulate plant material by the apparatus of claim 1, and adjusting the grinder setting as necessary so as to provide a target density for the particulate plant material.

15. The method of claim 14, wherein the grinder is a coffee bean grinder of the type used in a retail or a domestic environment.

16. The apparatus of claim 2, wherein the compression means is calibrated to a known compression force or is configured to be adjustable so as to allow a user-selectable compression force to be applied to the mass of particulate plant material disposed within the void of the vessel.

17. The apparatus of claim 4, wherein the vessel and/or the compression means comprises a user-comprehensible scale configured to allow a user to determine the volume occupied by a compressed mass of the particulate plant material within the void of the vessel.

18. The apparatus of claim 17 wherein the vessel and/or the compression means comprises a scale which is readable by reference to an edge or a marking on the vessel.

19. The apparatus of claim 5, wherein the void is one or more of (i) substantially circular in plan view, (ii) having a diameter similar or substantially identical to an extraction machine vessel used in a preparation of a liquor produced from the particulate plant material, and (iii) having a depth at least that of or similar or substantially identical to an extraction machine vessel used in a preparation of a liquor produced from the particulate plant material.

20. The apparatus of claim 8, wherein the weighing means is a balance having a tare function.

21. The apparatus of claim 8, wherein the density calculation means is embodied in application software executable on a processor-enabled device or on a mobile device.

22. The apparatus of claim 10, wherein the mass of particulate plant material is coffee and the apparatus is used to determine the density of one or more of whole bean, green bean, roast bean or ground bean.

23. The apparatus of claim 1, wherein the compression means is handleable by a user.

* * * * *